US008852580B2

(12) United States Patent
Schaefer et al.

(10) Patent No.: US 8,852,580 B2
(45) Date of Patent: Oct. 7, 2014

(54) METHOD AND DEVICE FOR SYNOVIAL CELL-CHARGED COLLAGEN MEMBRANE OR GEL

(75) Inventors: Birgit Schaefer, Schuepfheim (CH); Lothar Schloesser, Darmstadt (DE)

(73) Assignee: Geistlich Pharma AG, Wolhusen (CH)

( * ) Notice: Subject to any disclaimer, the term of this patent is extended or adjusted under 35 U.S.C. 154(b) by 0 days.

(21) Appl. No.: 13/614,003

(22) Filed: Sep. 13, 2012

(65) Prior Publication Data

US 2013/0011463 A1   Jan. 10, 2013

Related U.S. Application Data

(62) Division of application No. 12/091,147, filed as application No. PCT/IB2006/002980 on Oct. 23, 2006, now Pat. No. 8,293,225.

(60) Provisional application No. 60/729,213, filed on Oct. 24, 2005.

(51) Int. Cl.
| A61F 2/02 | (2006.01) |
| A61F 2/30 | (2006.01) |
| A61L 27/36 | (2006.01) |
| A61L 27/38 | (2006.01) |
| A61L 27/24 | (2006.01) |

(52) U.S. Cl.
CPC ......... *A61L 27/3852* (2013.01); *A61L 2430/06* (2013.01); *A61F 2/30756* (2013.01); *A61F 2002/30971* (2013.01); *A61F 2002/30761* (2013.01); *A61F 2002/30766* (2013.01); *A61L 27/36* (2013.01); *A61F 2210/0004* (2013.01); *A61F 2310/00365* (2013.01); *A61F 2002/30062* (2013.01); *A61F 2/3094* (2013.01); *A61L 27/24* (2013.01); *A61L 27/3817* (2013.01); *Y10S 623/901* (2013.01)
USPC ........... 424/93.7; 424/548; 424/423; 623/901

(58) Field of Classification Search
CPC ......... C12N 5/0652; A61F 2/02; A61L 27/00; A61L 27/38; A61L 27/52; A61L 27/24
See application file for complete search history.

(56) References Cited

U.S. PATENT DOCUMENTS

| 5,041,138 | A | 8/1991 | Vacanti et al. |
| 5,792,751 | A | 8/1998 | Ledley et al. |
| 5,876,444 | A | 3/1999 | Lai |
| 6,242,247 | B1 | 6/2001 | Rieser et al. |
| 6,387,693 | B2 | 5/2002 | Rieser et al. |
| 6,436,138 | B1 | 8/2002 | Dowd et al. |
| 6,464,729 | B1 | 10/2002 | Kandel |
| 6,730,314 | B2 | 5/2004 | Jeschke et al. |
| 2002/0013627 | A1 | 1/2002 | Geistlich et al. |
| 2002/0122790 | A1 | 9/2002 | Hunziker |
| 2003/0036797 | A1 | 2/2003 | Malaviya et al. |
| 2003/0039695 | A1 | 2/2003 | Geistlich et al. |
| 2004/0030404 | A1 | 2/2004 | Noll et al. |
| 2004/0030406 | A1 | 2/2004 | Ochi et al. |
| 2004/0133275 | A1 | 7/2004 | Mansmann |
| 2004/0249448 | A1 | 12/2004 | Gault |
| 2005/0043814 | A1 | 2/2005 | Kusanagi et al. |
| 2005/0043816 | A1 | 2/2005 | Datta et al. |
| 2005/0234549 | A1 | 10/2005 | Kladakis et al. |
| 2005/0288796 | A1 * | 12/2005 | Awad et al. ................ 623/23.72 |
| 2009/0186062 | A1 | 7/2009 | Spector et al. |
| 2009/0239282 | A1 | 9/2009 | Fabre et al. |

FOREIGN PATENT DOCUMENTS

| EP | 1283063 | | 2/2003 |
| JP | 63-198978 | A | 8/1988 |
| JP | 2000-107278 | A | 4/2000 |
| JP | 2001-224678 | A | 8/2001 |
| JP | 2001-293081 | A | 10/2001 |
| JP | 2003-160506 | A | 6/2003 |
| WO | 9518638 | | 7/1995 |
| WO | 9624310 | | 8/1996 |
| WO | 02060315 | | 8/2002 |
| WO | 2005/003331 | A1 | 1/2005 |
| WO | WO 2005/012512 | * | 2/2005 ............... C12N 5/06 |

OTHER PUBLICATIONS

Japanese Office Action issued in JP Appln. No. 2008-537214 on Jun. 26, 2012 along with English translation, 10 pages.
Japanese Office Action issued in JP Appln. No. 537214/2008 on Feb. 14, 2012 along with English translation, 11 pages.
Partial English translation of JP 63-198978, 2 pages, Aug. 17, 1988.
Yokoyama et al., "In vitro cartilage formation of composites of synovium-derived mesenchymal stem cells with collagen gel", Cell Tissue Res (2005) 322; pp. 289-298.
International Search Report dated Mar. 28, 2007 (PCTIIB2006/002980).
Guoping Chen et al., "Cell adhesion of bone marrow cells, chondrocytes, ligament cells and synovial cells on a PLGA-collagen hybrid mesh", Materials Science and Engineering C, vol. 24, No. 6-8, Dec. 1, 2004, pp. 867-873.
BD BioCoat & BD Falcon, Microporous Membrane Inserts & Cell-Based Assay Systems, 2004 Internet Article printed from www.bdbiosciences.com, 22 pages.

(Continued)

*Primary Examiner* — Allison Fox
(74) *Attorney, Agent, or Firm* — Rothwell, Figg, Ernst & Manbeck, P.C.

(57) ABSTRACT

An implant for repair of a cartilaginous defect in a subject includes a collagen matrix charged with synovial cells. A method preparing an implant for repair of a cartilaginous defect in a subject includes obtaining a fluid containing synovial cells and charging the synovial cells to the matrix. A device for preparing a cell-charged implant includes a first chamber and a second chamber, the first and second chambers being separated by a membrane and a perforated filter. The membrane is adapted to collect cells from a cell-containing fluid introduced into the first chamber and the perforated filter is adapted to permit passage or diffusion of the fluid through the second chamber. A method for preparing a cell-charged implant utilizes the device.

3 Claims, 4 Drawing Sheets

(56) References Cited

OTHER PUBLICATIONS

Serial Confocal Microscope Images of Trophoblast Cells Invading Through Matrigei-Coated Invasion Chambers, Jul. 15, 2004 Internet Article printed from http://web.archive.org/web/200407151 02130/ http://www.obsgynae.auckland.ac.nz/research/immunology/research_projects.htm, 3 pages.

James E. Greening et al., "Processing and Presentation of the Islet Autoantigen GAD by Vascular Endothelial Cells Promotes Transmigration of Autoreactive T-Cells", Diabetes, vol. 52, No. 3, Mar. 1, 2003, pp. 717-725.

E. B. Hunziker, "Articular cartilage repair: basic science and clinical progress. A review of the current status and prospects", Osteoarthritis and Cartilage, vol. 10, No. 6, Jun. 2002, pp. 432-463.

\* cited by examiner

METHOD AND DEVICE FOR SYNOVIAL CELL-CHARGED COLLAGEN MEMBRANE OR GEL

CROSS-REFERENCE TO RELATED APPLICATIONS

The present application is a divisional of U.S. patent application Ser. No. 12/091,147, filed on Apr. 22, 2008, which is a 35 U.S.C. §371 National phase Entry Application from PCT/IB2006/002980, filed Oct. 23, 2006, and designating the United States. This application also claims the benefit of U.S. Application No. 60/729,213, filed Oct. 24, 2005, the disclosure of which is incorporated herein in its entirety by reference.

FIELD OF THE INVENTION

The present invention relates to the field of cartilaginous defect repair.

DESCRIPTION OF THE BACKGROUND ART

All United States Patents and Patent Application Publications referred to herein are hereby incorporated by reference in their entireties. In the case of conflict, the present specification, including definitions, will control.

Compositions and methods for treatment of cartilage defects are known in the art. There remains a need in the art, however, for improved compositions and methods for repair of cartilaginous defects and for methods and devices for preparing such compositions.

SUMMARY OF THE INVENTION

In accordance with the present invention, an implant is provided for repair of a cartilaginous defect in a subject, wherein the implant comprises a collagen matrix charged with synovial cells. The invention also encompasses methods for preparing such implants, devices for preparing such implants and methods of preparing such implants with such devices.

DETAILED DESCRIPTION OF THE INVENTION

Figure 1:
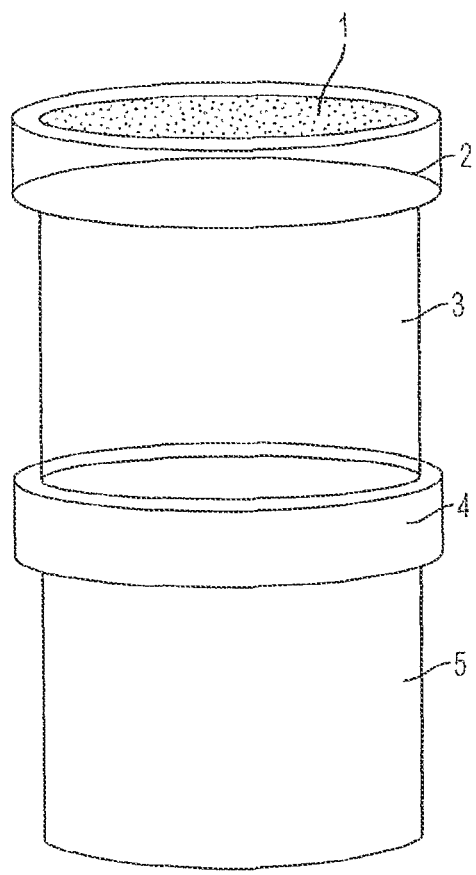
FIG. 1 depicts a device for preparing a synovial cell-charged implant in accordance with the invention.

The present invention relates to synovial cell-charged collagen membranes and gels, and methods and devices for producing and using the same.

In an aspect, the invention provides a membrane implant for repair of a cartilaginous defect in a subject in need thereof, the implant comprising a collagen membrane charged with synovial cells. The invention further provides a gel implant for repair of a cartilaginous defect in a subject in need thereof, the gel implant comprising a collagen gel containing synovial cells. The invention also provides methods of preparing the membrane implants and the gel implants described herein, and methods of repairing a cartilaginous defect in a subject by applying the implants to such a defect.

The present invention further provides a device for preparing a cell-charged membrane implant. In an embodiment, the device comprises a first chamber and a second chamber, the first and second chambers being separated by a membrane and a perforated filter, wherein the membrane is adapted to collect cells from a cell-containing fluid introduced into the first chamber, and wherein the perforated filter is adapted to permit diffusion of the fluid therethrough to the second chamber. The invention further provides methods of preparing cell-charged membrane implants by utilizing such devices.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes can be made without departing from the spirit or scope of the present invention.

In one embodiment, the present invention provides a membrane matrix implant for repair of a cartilaginous defect in a subject in need thereof, wherein the implant comprises a collagen membrane charged with synovial cells. The membrane may be any suitable thickness, e.g, within a range of about 0.1-5 mm, 0.1-1 mm, 0.1-0.5 mm, 0.5-1 mm, etc. According to one aspect, the membrane is capable of passing a liquid, such as synovial fluid, therethrough, either under gravity, or positive or negative pressure, while prohibiting passage of cells such as synovial cells therethrough, and collecting such cells in said membrane or on a surface thereof.

In embodiments of the invention, synovial fluid is removed from the synovial space of a joint, and cells from the synovial fluid are charged (loaded) onto the collagen membrane. The synovial fluid may be obtained from the subject in need of the cartilaginous repair. The synovial cell-charged collagen membrane then is applied to a cartilage defect for repair thereof.

Alternatively, synovial fluid can be mixed with collagen powder and formed into a gel matrix implant, which may be inserted into a cartilage defect for repair thereof. In certain embodiments, the end concentration of synovial cells in the implant is within in a range of about 0.000001-25% by weight.

Figure 4:
FIG. 4 schematically shows a membrane according to one embodiment.

A collagen membrane matrix for use in accordance with the present invention can be any suitable collagen membrane, including collagen membranes formed from collagen I, collagen II, collagen III, etc., including combinations thereof such as a collagen membrane comprising a mixture of collagen I/III (e.g., about 95% collagen I and 5% collagen III), and preferably is completely resorbable after implantation into a subject. A preferred membrane for use in accordance with the present invention is BioGide® or ChondroGide® from Ed. Geistlich Soehne AG fuer chemische Industrie. The BioGide® material is described in U.S. Pat. No. 5,837,278, incorporated herein by reference, and preferably is a sheet formed from peritoneum of cow or pig, preferably from young pig. As shown in FIG. 4, this collagen membrane 9 is comprised of a barrier layer having a smooth face 10 so as to inhibit cell adhesion thereon and act as a barrier to prevent passage of cells therethrough. Opposite the smooth face is a rough, fibrous face 12 allowing cell growth thereon. The synovial cells 14 preferably are charged to the fibrous face 12.

Figure 5:
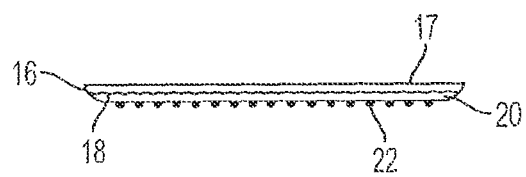
FIG. 5 schematically shows a membrane according to a second embodiment.

Other membrane matrices may be utilized, including membrane sheets formed substantially or predominately of collagen II, or a multilayer membrane as show in FIG. 5, such as a BioGide® membrane 16 (predominately collagen I/III) with smooth face 17 and fibrous face 18, to which is applied (e.g., adhered as a slurry and then freeze dried) a predominately collagen II matrix layer 20 on the fibrous face 18 of BioGide®. In this embodiment, the synovial cells can 22 can be deposited on the collagen II matrix layer of a multi-layer membrane as described above. Preferably, the synovial cell-charged collagen II matrix layer 20 is oriented toward the defect, with the smooth face 16 oriented away from the defect.

An implant according to the invention may contain glycosaminoglycans (GAGs) such as hyaluronic acid, chondroitin 6-sulphate, keratin sulphate, dermatan sulphate, etc., which serve to provide a natural medium in which serve to provide a natural medium in which cells can become embedded and grow. While it is possible to incorporate into the implant glycosaminoglycans from different sources which do not necessarily have the same composition, molecular weight and physiological properties as those from cartilage, preferred glycosaminoglycans are those extracted from cartilage itself.

Figure 6:
FIG. 6 schematically shows a gel implant according to a third embodiment.

The invention also provides a gel matrix implant 24 for repair of a cartilaginous defect in a subject in need thereof, wherein the implant comprises a collagen gel containing synovial cells 26 (see FIG. 6). The collagen in the gel implant preferably is completely resorbable in the subject, and can be any suitable collagen, and preferably comprises collagen I, collagen II, or collagen III, or mixtures or combinations thereof. The gel implant 24 may comprise a gel scaffold or gel sheet, and be any suitable thickness, e.g., about 1-10 mm, preferably about 5 mm. The gel implant may have a collagen end concentration of about 0.5% to about 4% by weight.

In other embodiments, the implant may comprise a multilayer implant including a collagen membrane as described above, to which is adhered a gel matrix as described in the previous paragraph. Thus, the implant comprises at least one of a collagen membrane or collagen gel, which may be in a form of a scaffold or a sheet.

The invention also provides a method of preparing a membrane implant for repair of a cartilaginous defect in a subject in need thereof, the method comprising obtaining a fluid containing synovial cells and charging the synovial cells onto a collagen membrane. In an embodiment, the fluid is synovial fluid obtained from a synovial space of a joint. The synovial cells may be obtained from minced synovial membrane.

The invention further provides a method of preparing a gel implant for repair of a cartilaginous defect in a subject in need thereof, the method comprising mixing a collagen powder with synovial fluid and forming into a gel implant. In an embodiment, collagen powder may be used in pure form (such as, for example, collagen I, collagen II, or collagen III) or in mixed form (such as, for example, collagen I and/or II and/or III), or mixed with other components of extracellular matrix, such as proteoglycans (such as, for example, hyaluronic acid or other GAGs as described above). The method may comprise incubating the collagen powder and the synovial fluid for a time sufficient to result in complete gelatinization.

The invention also provides methods of repairing a cartilaginous defect in a subject that include applying or inserting the implants described herein to the defect for the repair thereof. The subject can be any subject in need of cartilaginous defect repair, but is preferably a human subject. The repairing may comprise rebuilding a meniscus.

The invention also provides a device for preparing a cell-charged membrane implant. In a preferred embodiment, the device comprises a first chamber and a second chamber, the first and second chambers being separated by a membrane and a perforated filter, wherein the membrane is adapted to collect cells from a cell-containing fluid introduced into the first chamber, and wherein the perforated filter is adapted to permit passage or diffusion of the fluid therethrough to the second chamber. The perforated filter can comprise any suitable material, the selection of which is within the skill of one ordinarily skilled in the art. In preferred embodiments, the perforated filter comprises polyethylene or polypropylene. In an embodiment, the device can further comprise a filter pack in the second chamber, the filter pack being adapted to absorb the diffused fluid. The filter pack can comprise any material suitable for performing the intended function. In embodiments, the device further comprises a lid enclosing the first chamber. In preferred embodiments, the lid is adapted to permit the passage of fluid from a needle punctured therethrough. The lid can be any suitable material known to those of ordinary skill in the art. In preferred embodiments, the lid comprises rubber. In certain embodiments, the first chamber and the second chamber may be removably connected to each other. This can be accomplished by any suitable means, such as a band or ring-shaped structure surrounding the joint formed by the connection of the two chambers. The structure may include threads or other means of securing the chambers together during operation. In the alternative, the chambers can be connected by interlocking threads on the chambers, thus permitting them to be screwed together without a further connecting element. In preferred embodiments, the membrane is a collagen membrane. In alternate preferred embodiments, the cell-containing fluid is synovial fluid, containing synovial cells.

The invention further provides a method for preparing a cell-charged membrane utilizing a device described herein. In an embodiment, the method comprises providing a device comprising a first chamber and a second chamber, the first and second chambers being separated by a membrane and a perforated filter, and introducing a cell-containing fluid into the first chamber, wherein cells in the fluid are collected on the membrane and wherein the fluid is diffused through the membrane and the perforated filter, thereby resulting in a cell-charged membrane. In preferred embodiments, the membrane is a collagen membrane and the cells charged onto the membrane are synovial cells, contained in synovial fluid. In embodiments, the device further comprises a lid enclosing the first chamber, as described herein, and the method further comprises introducing the fluid into the first chamber with a needle inserted through the lid.

Accordingly, in an aspect of the invention, a synovial cell-charged collagen membrane is utilized as an implant for repair of cartilaginous defects. In an embodiment, synovial fluid is removed from the synovial space of a joint, and cells from the synovial fluid are charged (loaded) onto a collagen membrane, or a collagen gel containing the synovial cells is formed.

Figure 2:
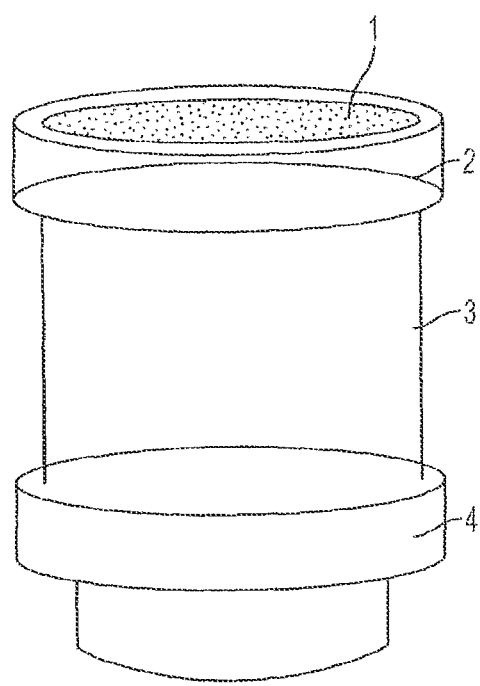
FIG. 2 depicts an upper portion of a device in accordance with the invention.
Figure 3:
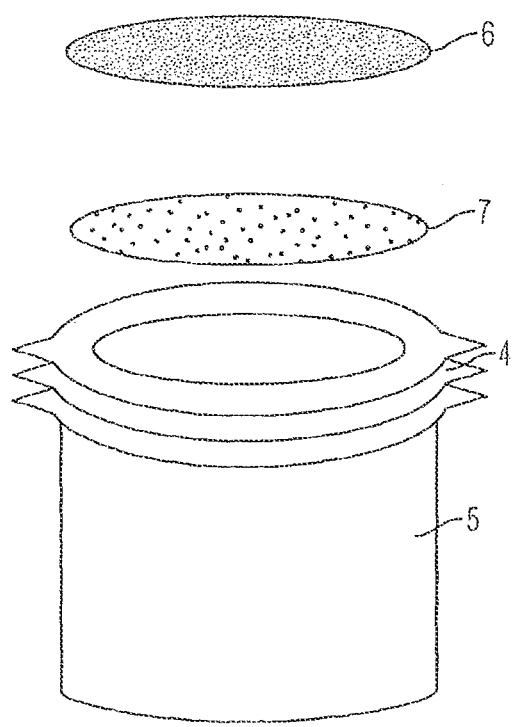
FIG. 3 depicts a lower portion of a device in accordance with the invention.

Referring now to the drawings, where like elements are designated by like reference numerals, FIGS. 1-3 illustrate preferred devices and aspects thereof, which can be utilized to prepare a cell-charged collagen membrane in accordance with the present invention. Thus, for example, the synovial cells (as described above) may be charged to a collagen membrane utilizing the device shown in FIGS. 1, 2 and 3. In accordance with the illustrated embodiments, for example, synovial fluid can be injected through a rubber lid 1 into a first or upper chamber 3 of the device. Synovial cells can be loaded onto the collagen membrane 6 at the bottom of the upper chamber 3 as synovial fluid is drawn through the collagen membrane 6 and perforated inert filter plate 7, the synovial fluid being absorbed into a second or lower chamber 5, which can be filled with filter material for absorption of the fluid. The filter material for absorption of the fluid can be tightly bound to the inert filter plate. The inert filter plate is preferably not reactive with the collagen membrane. The synovial cell-charged collagen membrane then is applied to a cartilage defect for repair thereof. Alternatively, synovial fluid can be mixed with collagen powder and formed into a gel implant, which may be inserted into a cartilage defect for repair thereof.

As depicted in the drawings, the device can include a fixing ring 2 to aid in securing the rubber lid 1 to the upper chamber and a means 4 for connecting the two chambers to each other during operation. Any suitable connection means can be used, including a separate device surrounding the joint formed by the two chambers when placed adjacent each other. In the alternative, the chambers can be connected by interlocking threads on the chambers, thus permitting them to be screwed together without a further connecting element.

The invention is further illustrated by the following examples, which are not intended to be limiting.

EXAMPLE 1

A method in accordance with one embodiment is as follows.

Synovial fluid contains fibroblast-like synovial cells with mesenchymal stem cell characteristics. Synovial fluid may be used in pure form or diluted e.g. 1:1 with sodium chloride solution. The method may include use of synovial fluid cells for cartilage regeneration be it fibrous or hyaline cartilage, be it as non-amplified cells or in vitro amplified cells. Synovial fluid is collected aseptically by aspiration. The fluid may be diluted 1:1 with DMEM/10%FCS medium, which is then put into a 25 $cm^2$ culture flask for cultivation of cells. Alternatively, the fluid may be diluted 1:5 with 1×PBS with Ca/Mg, centrifuged at 500×g for 5-10 minutes at room temperature. The supernatant is removed, the pellet resuspended in 10 ml DMEM/10%FCS, and the cell suspension transferred to a 25 $cm^2$ culture flask. Medium is changed after 24 hours of primary culture afterwards every 2-3 days. Cells are cultured until they reach 75% confluency. Cells are treated for 10 minutes with 3 ml treatment of 3 ml 0.02%EDTA with consequent treatment of 2 ml typsin/EDTA 0.1%/0.02 until cells are completely detached. Trypsination is stopped with 10 ml DMEM/10%FCS or alternatively with 1 m 1× soybean inhibitor. Cell suspension is centrifuged at 500×g, 5 minutes at room temperature. Pelleted cells are transferred to a new flask.

As noted above, the device and aspects thereof depicted in FIGS. 1-3 can be utilized in accordance with the invention to load or charge cells on a collagen membrane. The upper chamber 3 may hold a total amount of about 50-60 ml synovial fluid mixed e.g. 1:1 with sterile sodium chloride solution. The mixture, in the described embodiment, is injected via a syringe needle through a rubber lid 1. Upper 3 and lower 5 chambers are separated via a collagen membrane 6 and an underlying perforated inert filter 7, that allows diffusion of the fluid into an underlying filter pack. The capacity of this filter for absorption of the fluid may be about 60 ml. The inert filter plates 7 may be, e.g., of polyethylene or polypropylene. Pore size may be e.g. 1 mm in diameter. Pores may be localized every mm (e.g., 5 pores per 1 cm). Suitable diameters of the membranes 6 are adapted to the diameter of the seeding device e.g., about 2 cm-5 cm. The seeding system may have different volumes, since the amount of synovial fluid is not the same in all joints. 2-5 ml, 20-30 ml and 50-60 filling are examples. This device can be used for any kind of seeding of cells (be it the seeding of freshly isolated cells of the patient or cells cultured prior to application).

The two chamber system (upper chamber 3 with lid 1, that can be punctured by syringe needle, lower chamber 5 with filter 7, collagen membrane 6 in between, e.g., BioGide®/ChondroGide® with rough surface toward the upper chamber 3) is filled with aspirated sterile synovial fluid or mixture. The synovial fluid phase passes through the collagen membrane 6 and filter plate 7, leading to the deposition of synovial cells on collagen membrane 6, e.g., the rough side of BioGide®. As noted above, other collagen membranes may be used, such as the SIS-membrane from Cook, paraguide membranes or hyaluronic acid membranes such as Hyatt®. Alternatively, collagen II gel may be used to rebuild menisci utilizing minced pieces of a synovial membrane biopsy, which has been harvested during an operation procedure.

It is preferable to wait at least 30 minutes to allow adherence of cells on the membrane. As noted above, the synovial fluid can be diluted with physiological sodium chloride solution to accelerate absorption of the gelatinous synovial fluid.

The synovial cell-charged collagen membrane then is applied to a chondral/meniscal defect for repair thereof. When BioGide®/ChondroGide® is utilized, the cell-charged rough side is oriented toward the defect, with the smooth side oriented away from the defect and toward the joint space.

EXAMPLE 2

Another embodiment of the invention utilizes powdered collagen, e.g., collagen I/III for the production of synovial fluid gel for cartilage repair, as described in the present example.

In this example, synovial fluid is aspirated aseptically as above.

The synovial fluid is transferred into a chamber that contains collagen powder, which induces gelatination. The use of collagen powder to induce gelatination of synovial fluid (e.g. 30 ml) may be in a round one chamber system (4.5 cm diameter, height 2 cm, lid like in the device presented herein, collagen powder preapplied in chamber). This system yields round gels (diameter: 4.5 cm, height 5 mm) with a collagen end concentration 0.5-4%. Collagen powder may be used in pure form (collagen I, II or III), mixed (collagen I and/or II and/or III) or mixed with other components of extracellular matrix such as proteogylcans (hyaluronic acid or other GAGs). The amount of collagen powder depends on the size of the gel needed for reconstruction of the cartilage. The collagen powder may be, e.g., 50-100% collagen, with the balance being other ECM components such as proteoglycans. The collagen end concentration may be 0.5-4% by weight. Incubation temperature may be room temperature, and duration may be at least about 30 minutes. The synovial cells in the final round gels may vary from patient to patient, depending on the member of cells harvested from the patient. In this embodiment, synovial fluid is mixed with collagen powder and the chamber is incubated horizontally until gelantination is complete.

The synovial cell-charged collagen gel then is implanted into a cartilaginous defect for repair thereof.

What is claimed:

1. A method of preparing an implant for repair of a cartilaginous defect in a subject, said method comprising mixing a fluid containing synovial cells with a collagen powder to form a gel implant from said mixture of fluid containing synovial cells and collagen powder, further comprising incubating said collagen powder and said synovial fluid for a time sufficient to result in complete gelatinization of said gel implant, and further comprising adhering said gel implant to a collagen membrane to form a multilayer implant.

2. The method of claim 1, wherein the gel implant comprises a collagen gel, said gel comprising at least one of collagen I, collagen II or collagen III.

3. A method of repairing a cartilaginous defect in a subject, said method comprising:
   a) preparing a gel implant for repair of a cartilaginous defect in a subject, said method comprising mixing a fluid containing synovial cells with a collagen powder to form a gel implant from said mixture of fluid containing synovial cells and collagen powder, further comprising incubating said collagen powder and said synovial fluid for a time sufficient to result in complete gelatinization of said gel implant, and further comprising adhering said gel implant to a collagen membrane to form a multilayer implant; and
   b) applying said gel implant to the cartilaginous defect.

* * * * *